United States Patent [19]

Mathew et al.

[11] 4,400,527

[45] Aug. 23, 1983

[54] PRODUCING OXIMINOSILANES, OXIMINOGERMANES AND OXIMINOSTANNANES

[75] Inventors: Chempolil T. Mathew, Randolph; Harry E. Ulmer, Morristown, both of N.J.

[73] Assignee: Allied Corporation, Morris Township, Morris County, N.J.

[21] Appl. No.: 331,694

[22] Filed: Dec. 17, 1981

[51] Int. Cl.$^3$ ............................ C07F 7/10; C07F 7/22; C07F 7/30
[52] U.S. Cl. ............................... 556/422; 260/429 R; 260/429.7
[58] Field of Search .................. 260/429 R, 429.7; 556/422

[56] References Cited

U.S. PATENT DOCUMENTS 3,189,576 6/1965 Sweet ................................ 260/46.5
3,576,905 4/1971 McKeller et al. ................. 260/825
4,033,991 7/1977 Shinohara et al. ............ 260/448.2 E
4,126,630 11/1978 Müller et al. ................. 260/448.2 E

FOREIGN PATENT DOCUMENTS 176704 9/1976 Czechoslovakia .
435243 11/1974 U.S.S.R. .
494384 8/1976 U.S.S.R. ............................ 556/422
724514 11/1977 U.S.S.R. .
547245 5/1981 U.S.S.R. .

OTHER PUBLICATIONS

L. J. Tyler, letter entitled "Ketoxime dangers," Chemical and Engineering News, p. 3 (Sep. 2, 1974).

Primary Examiner—Paul F. Shaver
Attorney, Agent, or Firm—Alan M. Doernberg; Gerhard H. Fuchs

[57] ABSTRACT

A Group IVa metal halide such as methyl trichlorosilane is reacted with an oxime compound such as methyl ethyl ketone oxime in the absence of a base to form in high yields a product oximinosilane, oximinogermane or oximinostannane (e.g. methyl tris(methyl ethyl ketoximo)silane) and a by-product oxime hydrohalide. The oxime above that found in the product may be recovered by neutralization of the by-product oxime hydrohalide.

16 Claims, 1 Drawing Figure

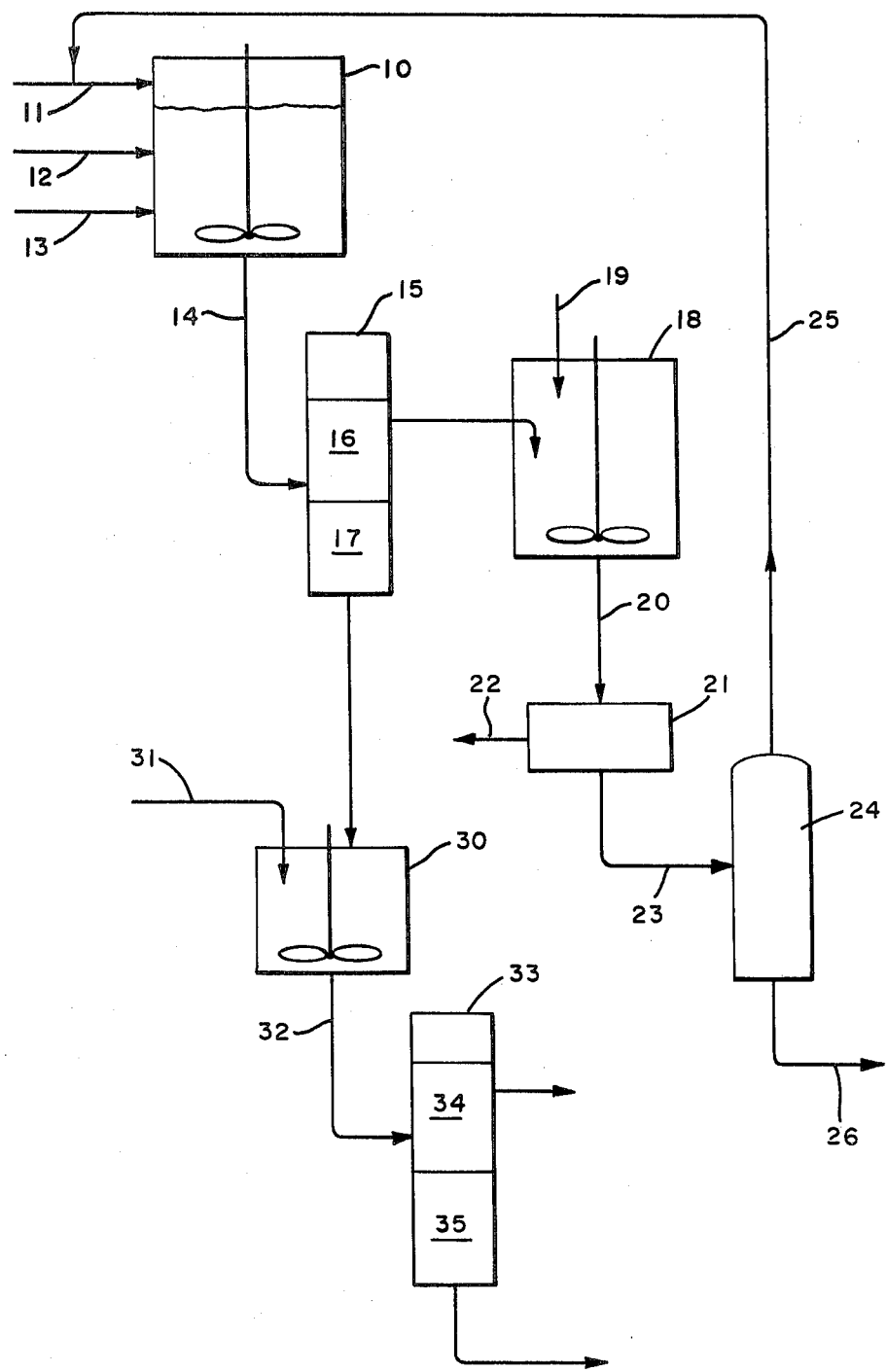

PRODUCING OXIMINOSILANES, OXIMINOGERMANES AND OXIMINOSTANNANES

DESCRIPTION

BACKGROUND

The preent invention relates to the production of oximinosilanes, oximinogermanes and oximinostannanes such as methyl tris(methylethylketoximino) silane, and especially for the production of such materials from alkyl and alkenyl chlorosilanes such as methyltrichlorosilane and vinyl trichlorosilane.

The classical method of preparing oximinosilanes is to react a chlorosilane such as methyl trichlorosilane with a stoichiometric amount of an oxime compound such as methyl ethyl ketoxime and a stoichiometric amount of an organic base such as triethylamine. In such process, the product and the hydrochloride of the organic base must be separated one from the other, normally requiring a distillation. Difficulties have been encountered in distilling the product from the organic base hydrochloride, with explosions sometimes resulting. A variation of this process described in U.S. Pat. No. 4,126,630 involves first reacting the chlorosilane with the amine to form an intermediate, and then reacting the intermediate with oxime compound.

An alternate process which has been suggested is to react the chlorosilane with a stoichiometric amount of the sodium salt of the oxime compound (e.g. methyltrichlorosilane reacted with three moles of sodium salt of methyl ethyl ketoxime). While the by-product inorganic salt (sodium chloride) is insoluble in the oximinosilane product, it remains difficult to separate because the sodium chloride is finely dispersed in the product. Furthermore, the sodium salt of the oxime compound requires the relatively expensive sodium metal to be used in its preparation.

A. Singh et al., in *J. Chem. Soc. Dalton Trans.*, vol. 17, pp. 1911-1913 (1972); *J. Organometallic Chem.*, vol. 57, pp. 301-311 (1973); *Ind. J. Chem.*, vol. 12, pp. 851-854 (1974); *Syn. React. Inorg. Metal-Org. Chem.*, vol. 4, pp. 549-556 (1974); and *Ind. J. Chem.* vol. 13, pp. 1197-1199 (1975) disclose the above three processes applied to the production of various oximinosilanes, oximinogermanes and oximinostannanes.

Russian Pat. No. 435,243 (1974) to G. V. Ryasin discloses a process of reacting an oxime compound with an organochlorosilane in the presence of a metal catalyst at 90° C. or above, stripping the byproduct HCl off with an inert gas. Russian Pat. No. 724,514 (1977) discloses the same process performed in a column with reduced residence times to avoid explosive decomposition of the product. See also Chem. Abstr. 91:20702n of Czeck Pat. No. 176,704.

BRIEF DESCRIPTION OF THE INVENTION

It has been found that oximinosilanes can be obtained in high yields from the direct reaction of the halosilane with oxime in the absence of additional reactants, by using at least two times the stoichiometric amount of oxime compound. In such a process, the by-product is the hydrochloride of the oxime compound (e.g. methyl ethyl ketoxime hydrochloride). It is believed that similar high yields will be obtained by the reaction of analogous halogermanes (germanium halides) and halostannanes (tin halides) with at least twice the stoichiometric amount of oxime compounds.

Accordingly, the present invention includes a process for the production of Group IVa metal oximates (i.e. oximinosilanes, oximinogermanes and oximinostannanes) which comprises reacting in the liquid phase a Group IVa metal halide (i.e. halosilane, halogermane or halostannane) of the formula $R_{4-n}MX_n$ with an oxime compound of the formula R'R"C=NOH at a mole ratio of oxime compound to Group IVa metal halide of at least 2n:1; and separating the product of the formula

$(R'R''C=NO)_nMR_{4-n}$ from the by-product oxime hydrohalide of the formula R'R"C=NOH.HX; wherein R is alkyl of 1-6 carbons, alkenyl of 2-6 carbons, aryl, aralkyl, cycloalkyl, halogensubstituted forms thereof; M is Si, Ge or Sn; X is Cl, Br, or I; n is 1 to 4; and R' and R" are each independently H, alkyl of 1-6 carbons, aryl, cycloalkyl or aralkyl, or any of them substituted by halo, or R' and R" are together $(CH_2)_m$ wherein m is 3 to 7, or alkyl and halo-substituted forms thereof. Preferred such compounds are those wherein R is methyl, ethyl, phenyl or vinyl, wherein X is Cl and wherein n is 3. The reaction may be done either in the presence of a solvent or with neat reactants; and, depending upon the by-product oxime hydro-halide, the separation may be done by either phase separation or filtration.

DETAILED DESCRIPTION OF THE INVENTION

The two reactants in the present invention are the halosilane, halogermane or halostannane and the oxime compound. In some of the description that follows, reference will be made to the silicon-containing compounds without specific mention of the germanium-containing and tin-containing counterparts; but it should be understood that the entire description is intended to apply to these analogous compounds as well. Suitable halosilanes may be represented by the formula $R_{4-n}SiX_n$. In this formula R may be alkyl of 1-6 carbons such as methyl, ethyl, propyl, isopropyl, butyl, pentyl, or hexyl; may be alkenyl of 2-6 carbons such as vinyl, 2-propenyl, 3-butenyl or 2-pentenyl; may be aryl such as phenyl; may be aralkyl such as benzyl, or may be halosubstituted forms of any of these. Furthermore, different R's on the same molecule may differ, as in methyl ethyl dichlorosilane. Preferred substituents R are methyl, ethyl, vinyl and phenyl; with methyl and vinyl being most preferred. In the above formula X may be Cl, Br or I, and is preferably Cl. Also in the above formula n may be 1, 2, 3 or 4, but is preferably 3 such that there is one R and three X's.

Representative Group IVa metal halides which may be reacted with oxime compounds in the present process include methyl trichlorosilane, phenyl trichlorosilane, vinyl trichlorosilane, dimethyl dichlorosilane, trimethyl chlorosilane, methyl ethyl dichlorosilane, 2-chloroethyl trichlorosilane, triisobutyl germanium chloride, silicon tetrachloride, tri-n-butyl germanium iodide, diethyl dichlorosilane, triethyltin bromide, di-n-butyltin dichloride, triethyl chlorosilane, benzyl trichlorosilane, allyl trichlorosilane, trimethyl bromosilane, trimethyltin chloride, triphenyl silyl chloride, diphenyl germanium dichloride, methyl germanium trichloride, divinyltin dichloride and methyltin trichloride. Preferred are Group IVa metal halides wherein M is Si, wherein n is 3 and wherein R is alkyl (e.g. methyl and ethyl) or alkenyl (e.g. vinyl).

The oxime used in the present process may be any compound of the formula R'R"C=NOH. In this formula R' and R" may each be H or alkyl of 1–6 carbons, aryl, cycloalkyl, aralkyl; or any of these substituted by halogen; or R' and R" may together be $(CH_2)_m$ wherein m is an integer from 3 to 7; or R' and R" may together be such a group substituted by alkyl or halogen. If R' or R" or the two together are substituted by halogen, then the molecule should be one in which the halogen is not reactive (e.g. halogen on a tertiary carbon). Thus suitable oximes include 4-methylcyclohexanone oxime, 4-chlorocyclohexanone oxime, acetophenone oxime, benzophenone oxime, benzyl ethyl ketone oxime, cyclohexyl methyl ketone oxime and benzaldehyde oxime. Preferred oxime compounds include formaldehyde oxime, acetaldehyde oxime, acetone oxime, methyl ethyl ketone oxime, diethyl ketone oxime and cyclohexanone oxime; with methyl ethyl ketone oxime and acetone oxime being more preferred. Methyl ethyl ketone oxime is most preferred because of its use in many oximinosilane compounds used as room temperature vulcanizing agents for silicone polymers.

In the practice of the present invention, the mole ratio of oxime compound to halosilane is at least 2n:1, and is preferably not more than 3n:1, with mole ratios less 10 percent greater than 2n:1 (i.e. 2.2n:1) being more preferred. In the case of halosilanes wherein n is 3, this translates into a mole ratio between 6:1 and 6.6:1. For the reaction between methyltrichlorosilane and methyl ethyl ketone oxime, the mole ratio may be as high as 10:1 or more, but is preferably 9:1 or less (to maintain a clear phase separation) and is more preferably between 6:1 and 6.6:1.

The reaction may be done either with neat reactants or in the presence of a solvent. It has been found that an inert hydrocarbon solvent such as hexane, petroleum ether, toluene, or other similar low-boiling materials may be advantageously used in order to lower the viscosity of the reaction mixture and to lower both the viscosity and the density of the product oximinosilane-containing phase so as to facilitate the separation of the oximinosilane from the oxime hydrohalide, which may be either a solid or a heavier liquid. Under such circumstances, the proportion of solvent to various reactants is not critical, with greater amounts of solvent acting to increase the ease of separation, but requiring additional evaporation or distillation to remove the solvent from the product after separation of the product from oxime hydrohalide by-product. For any particular system, the amount of solvent preferably used can be easily determined; and in the system of methyltrichlorosilane reacted with methyl ethyl ketone oxime, a suitable ratio of solvent to methyltrichlorosilane is between about 1:1 and 2:1 by weight.

The temperature at which the reaction occurs is not critical, with the reaction occurring reasonably rapidly at room temperature or below, and with increasing speed but with some increase in formation of color bodies as the temperature increases. While a temperature range from about 0° C. to about 100° C. is generally suitable, it is preferred, at least in the case of the reaction between methyltrichlorosilane and methyl ethyl ketone oxime, to operate between about 20° C. and about 70° C. Because the reaction is exothermic, a temperature at the higher end of this range can normally be achieved by introducing the reactants at room temperature and, without extensive heat exchange, allowing the reaction mixture to heat up to a temperature of 30° to 60° C. The time of the reaction is also not critical, with reaction times (in the case of batch processes) and residence times (in the case of continuous processes) generally being in the range of 5 minutes to 5 hours, and especially 30 minutes to 2 hours. It will be appreciated that a suitable reaction time can be determined by routine experimentation for any particular set of reactants, solvent, temperature and other operating conditions.

Once the reaction is completed, the product, the by-product oxime hydrohalide, the solvent and any unreacted oxime compound will generally separate into two phases which are either two liquid phases or a liquid phase and a solid phase at room temperature or above. The first or organic phase (which is usually the top phase) will contain essentially all the solvent, essentially all of the product oximinosilane, most of the unreacted oxime compound and only minor amounts of the by-product oxime hydrohalide. The second phase, which may be either a liquid (generally the bottom phase) or a solid, will contain the by-product oxime hydrohalide, with small or trace amounts of solvent, product oximinosilane and unreacted oxime compound. The phases may be separated by any conventional technique, such as by decantation, filtration, centrifugation or other conventional techniques for separating solids from liquids or for separating two liquids of different densities. In general, relatively little time is required for the two phases to separate in essentially clean fashion.

Once the phases are separated, the product is recovered from the organic phase. One suitable method of purifying the product, especially of any by-product oxime hydrohalide, is to add to this organic phase a dry basic compound, which is preferably ammonia gas, so as to neutralize any oxime hydrohalide and generate inorganic halides (e.g. ammonium chloride) which forms an insoluble precipitate and free oxime compound. The solid inorganic halide is then removed (e.g. by filtration or centrifugation), while the solvent, any unreacted oxime compound and any oxime compound generated by the dry base are removed from the organic phase by flash evaporation, distillation or other similar technique which takes advantage of the relatively low boiling point of both the solvent and the oxime compound relative to the product oximinosilane. It is preferred that this evaporation be conducted at subatmospheric pressures, e.g. below 10 kPa, so as to minimize the temperature to which the product oximinosilane is exposed. Thereafter, after an optional filtration to remove any solids which may have formed or accumulated during the evaporation step, the product is ready for use. It will be appreciated that, depending upon that R and n are, the products can be useful in a variety of applications, and especially as room temperature vulcanizing or curing agents for silicones. It is not required to distill the product oximinosilanes as an overhead from any feed, but rather through the combination of filtration and evaporation of solvent and oxime compound, a relatively pure oximinosilane may be produced.

In the separation of the reaction mixture, a second phase is formed containing principally oxime hydrohalide by-product. It is highly desirable to recover this material in useful form either for recycle to the reaction or otherwise. This material, after whatever purification may be required, may be used for the production of hydroxylamine salts, preferably in a manner of U.S. patent application Ser. No. 295,347, filed Aug. 24, 1981 of Bonfield et al. If, however, it is desired to regenerate oxime compound from this oxime hydrohalide, the preferred method is to mix this second phase with a base, so as to generate a salt (preferably an inorganic salt) and a free oxime compound. One contemplated method for conducting this neutralization is to add a dry base, and especially ammonia gas, to the second phase until a moderate pH, (e.g. pH 7) is achieved. Under these conditions large amounts of ammonium chloride or other ammonium halide will form as a precipitate in the oxime compound. By filtration or otherwise, the ammonium salt may be removed; and a dry oxime compound is then left, which may be recycled to the main reaction with halosilane. It is desirable in conducting such a neutralization with ammonia to thoroughly agitate the slurry as it forms so as to neutralize as much of the oxime hydrohalide as possible. It will be appreciated, however, that any oxime hydrohalide remaining in the oxime compound would be recycled and be relatively inert in the reaction mixture.

An alternate method of neutralizing the oxime hydrohalide is to add an aqueous base solution such as aqueous ammonium hydroxide, aqueous sodium hydroxide, aqueous potassium hydroxide or the like so as to form an aqueous salt solution, which phase separates from an oxime compound. It is desirable in such a neutralization process to either use aqueous base of proper concentration, or to have a separate feed of water in proper ratio, to enable the mixture after neutralization to separate and form a saturated salt solution at the temperature involved (e.g. 25 percent sodium chloride at room temperature). The second layer would contain the oxime compound (e.g. methyl ethyl ketone oxime); and the solubility of the oxime compound in the saturated aqueous phase would then be minimized.

While neutralization with aqueous base is a generally easier procedure to follow, because of the ease of mixing, lower viscosity, and absence of solids, it has the disadvantage that it produces an oxime compound containing some dissolved water. Depending upon the use to which the oxime compound is to be put, the water may be removed by passage through a drying agent, distillation, azeotropic distillation or other techniques. If the intention is to recycle the oxime compound to the reaction with halosilane, it is desirable to remove the water from the oxime compound first, preferably down to levels of less than 1000 ppm.

FIG. 1 illustrates a preferred embodiment of the process of the invention wherein reactor 10 is equipped with agitation and covered with an inert atmosphere (e.g. nitrogen) to assure reasonably anhydrous conditions. A solvent such as petroleum ether or hexane is fed in stream 11 to reactor 10. An oxime such as methyl ethyl ketone oxime (MEKO) is fed in stream 12 to reactor 10. A halosilane such as methyltrichlorosilane (MTCS) is fed in stream 13 to reactor 10. All three streams should be essentially water-free (e.g. less than 1000 ppm water). The molar ratio of MEKO to MTCS should be maintained at 6:1 or higher, and preferably about 6:1 to 6.6:1.

Reactor 10 may be operated in batch, semicontinuous or continuous fashion with a residence time of about 0.5-2 hours. In batch operation an initially empty reactor 10 is charged with all three feeds and the reaction mixture is agitated for the desired period. Because of the reaction heat generated, some cooling may be applied by indirect cooling of the vessel or bleeding off solvent vapor, so as to limit the temperature to about 30°-60° C. at maximum. After the reaction period, reaction mixture is removed from reactor 10 in stream 14 to separation vessel 15.

In continuous operation, as reaction mixture is removed through stream 14, additional solvent, MEKO and MTCS are added in approximately the same proportions as the initial charge, with the feed rates of streams 11, 12, and 13 matching the withdrawal rate in stream 14 (which may be an overflow) and with an average residence time at the desired 1-3 hour level.

Various combinations of batch and continuous operation will be apparent from the above to one skilled in the art, and the present invention is not limited to any particular form. In addition, the reaction may be conducted under plugflow conditions, such as in a pipe.

In separation vessel 15, a phase 16 consisting essentially of product oximinosilane (e.g. methyl tris(methyl ethyl ketoximino) silane or MMEKOS) and solvent will separate quickly and cleanly from a phase 17 consisting essentially of oxime hydrohalide (e.g. methyl ethyl ketone oxime hydrochloride or MEKOHC). Since MEKOHC is a liquid at room temperature, phase 17 is illustrated in the figure as a liquid phase heavier than phase 16. For other oxime hydrohalide by-products (e.g. acetone oxime hydrochloride or cyclohexanone oxime hydrochloride), phase 17 is a solid such that separation vessel 15 is a centrifuge, filtration system or other similar liquid/solid separation device. Phases 16 and 17 are removed from vessel 15 continuously or intermittently and further treated as described below. A representative composition for phase 16 is over 40% MMEKOS, about 40% solvent, under 2% MEKOHC, under 2% MEKO and minor amounts of various by-products such as dimers and trimers of MMEKOS. A representative composition for phase 17 is over 95% MEKOHC, under 2% solvent, under 2% MMEKOS and under 2% MEKO.

Phase 16 is removed from separation vessel 15 to treatment vessel 18, equipped with agitation, where it is treated with dry ammonia gas fed in stream 19 in an amount sufficient to convert the MEKOHC to MEKO and ammonium chloride. Residence times in treatment vessel 18 of only a few minutes are required, but longer times may be used. The resultant thin slurry is withdrawn from treatment vessel 18 in stream 20 to filtration device 21 where the solid ammonium chloride is removed from the liquid. Periodically, the crude solid ammonium chloride is removed from filtration device 21 as shown by stream 22 for disposal or separation into organic and inorganic materials. A representative composition of the clarified stream 23 downstream of filtration device 21 is over 40% MEEKOS, about 40% solvent, under 0.01% MEKOHC, 3-4% MEKO and minor amounts of dimers and trimers of MMEKOS.

The clarified stream 23 is fed to vacuum stripper 24 where it is separated at subatmospheric pressure into a vapor stream 25 containing essentially all of the solvent and MEKO, and a liquid bottom stream 26 containing the purified MMEKOS. Stream 26 may be again filtered to remove any solids that form upon solvent evaporation (e.g. precipitated dimers and trimers of MMEKOS) or may be used as taken from stripper 24. Because of the large boiling point differences between solvent (hexane=78° C. at 101 kPa) and MEKO (152° C. at 101 kPa) versus MMEKOS (above 300° C. at 101 kPa, 110° C. at 0.5 mm mercury or 67 Pa), a single plate is sufficient for stripper 24. If the temperature of about 50° C. of stream 14 is maintained by stream 23, no further heating is required in stripper 24.

Phase 17 in separation vessel 15 (containing mainly MEKOHC) is fed continuously or intermittently to neutralization vessel 30 equipped with agitation. Aqueous base (e.g. 17% NaOH) is fed to vessel 30 in stream 31 in proportions producing in vessel 30 a suspension of an aqueous phase containing saturated inorganic salt (e.g. NaCl) and an organic phase consisting of oxime compound (MEKO). This slurry is fed in stream 32 continuously or intermittently to a separation vessel 33 where it quickly and easily separates into oxime phase 34 and aqueous salt phase 35, both of which are removed. Aqueous phase 35 is cleared of residual organics in a conventional fashion and disposed of. Oxime phase 34, containing some water, may be purified in conventional fashion for use in a variety of processes requiring dry oxime (e.g. for recycle to stream 12) or used in wet form in other processes (e.g. for the production of hydroxylammonium chloride).

The present invention is illustrated by the following examples which, though conducted on a laboratory scale, are easily transferable to processes such as the one illustrated in FIG. 1.

EXAMPLE 1

Reaction of Methyl Ethyl Ketoxime with Methyl Trichlorosilane (6:1)

In a 100 mL 3-necked flask equipped with condenser, thermometer and dropping funnel was placed freshly distilled methyl ethyl ketoxime (MEKO) (52.5 g; 0.6 mol). A drierite tube was attached to the condenser to maintain a dry reaction medium. With stirring using a magnetic bar and cooling in an ice-water bath, methyl trichlorosilane (MTCS) (15 g; 0.1 mol) was added dropwise to the oxime. Temperature was maintained between 5° and 15° C. throughout the addition. When addition was complete, the ice bath was removed and the flask was heated over a mantle for 3 hours, with stirring and the temperature was maintained at 70°–85° C.

On cooling two distinct phases separated out. The colorless top phase was decanted using dry toluene (100 mL). The toluene solution was treated with ammonia gas, and a white precipitate of ammonium chloride was formed. The solid was filtered off and the clear filtrate distilled under reduced pressure.

A colorless liquid was collected at 105°–108° C./0.7 mm Hg (93 Pa). The yield was 23.4 g (77.7%). Carbon-13 and proton NMR of this sample showed that it was pure methyl tris-(methyl ethyl ketoximo)-silane.

EXAMPLE 2

Reaction of MEKO with MTCS (6:1)

In a 2-liter 3-necked flask fitted with condenser, thermometer and dropping funnel was placed MEKO (630 g) dissolved in hexane (450 g). With stirring, methyl trichlorosilane (180 g) was dropped started at 22° C. When the addition was completed (1 hour), the temperature had risen to 60° C. The mixture was heated at 70° C. with stirring for 2 hours, and then cooled to 20° C. The viscous bottom phase (468 g) was separated from the colorless mobile top phase (780 g).

The top phase was treated with ammonia gas from a cylinder (1 minute bubbling) and the solid ammonium chloride (16.4 g) was removed by filtration. The clear filtrate (752 g) was subjected to vacuum distillation to remove all the hexane and any unreacted MEK Oxime at a maximum of 100° C. and 1 mm Hg (133 Pa) pressure. The colorless liquid in the distillation flask (322 g, 89.4%) was analyzed by Carbon-13 NMR and found to be pure methyl tris-(methyl ethyl ketoximo)-silane.

The bottom phase on neutralization with aqueous sodium hydroxide gave methyl ethyl ketoxime (343 g after drying).

EXAMPLE 3

Reaction of MEKO with MTCS (6:1)

In a 2 liter 3-necked flask was placed methyl ethyl ketoxime (630 g) with petroleum ether (50°–110° C. boiling point range) (500 g). With vigorous stirring methyl trichlorosilane (180 g) was added slowly over 1 hour, when the temperature rose from 23° to 55° C. It was then heated with stirring for 2 hours at 65° C. After cooling to ambient temperature, the phases were separated.

The top phase (824 g) was treated with ammonia gas for 1 minute and filtered (11.5 g solid). The filtrate (850 g) was distilled to remove the solvent first at atmospheric pressure and any methyl ethyl ketoxime at reduced pressure (1 mm Hg or 133 Pa) at a maximum of 130° C. The liquid residue with a light amber color in the distillation flask weighed 326 g (90.6% yield) and was found to be pure methyl tris-(methyl ethyl ketoximo)silane.

The bottom phase (480 g) was then mixed with water (400 g) and neutralized (pH 7.0) with 50% aqueous NaOH (265 g). Methyl ethyl ketoxime was separated as the top phase and dried (341 g).

EXAMPLE 4

Reaction of MEKO with MTCS (6:1)

A one liter 3-necked flask was fitted with condenser, thermometer and dropping funnel, and a solution of methyl ethyl ketoxime (315 g) in dry toluene (400 mL) was placed in it. Methyl trichlorosilane (90 g) was then added slowly over 1 hour with stirring, and with no outside cooling. The mixture at 55° C. at the end of addition was heated further for 2 hours at 60° C. After cooling down to 40° C., the two phases were separated.

The bottom phase (292 g) was mixed with water (250 g) and 50% NaOH (112 g) to neutralize (pH 7.0). The top organic phase of methyl ethyl ketoxime was separated (239 g) which on drying furnished 230 g of oxime.

The top phase from the first step (407 g) was treated with ammonia gas and centrifuged to separate the small amount of ammonium chloride that separated. The raffinate was first subjected to distillation at atmospheric pressure to remove most of the toluene (pot temperature 120° C.). Then vacuum was applied (1 mm Hg or 133 Pa) to remove any unreacted methyl ethyl ketoxime. The liquid residue in the distillation flask (114 g, 63.3% yield) was brown in color, but was found by Carbon-13 NMR to be pure methyl tris-(methyl ethyl ketoximo)silane.

EXAMPLE 5

Neat Reaction of MEKO with MTCS (6:1)

In a one liter 3-necked flask fitted with condenser, thermometer and dropping funnel was placed methyl ethyl ketoxime (315 g). Methyl trichlorosilane (90 g) was added dropwise with no cooling over a period of 1 hour. Temperature rose from 24° C. to 60° C. and phases separated out. The bottom phase (258 g) of the oxime hydrochloride was mixed with water (250 mL) and then neutralized (pH 7.0) with 50% NaOH solution (120 g). The top phase of methyl ethyl ketoxime on drying weighed 159 g.

The top phase from the first stage (133 g) was treated with ammonia gas and the solid ammonium chloride formed filtered off to furnish a clear, colorless liquid, which was heated at 100° C. for 2 hours at reduced pressure (1 mm Hg or 133 Pa) to remove small amounts of methyl ethyl ketoxime. The undistilled portion was a colorless liquid (127 g, 70.5% yield), which was pure methyl tris(methyl ethyl ketoximo)silane.

EXAMPLE 6

Reaction of MEKO with MTCS (6:1)

Methyl ethyl ketoxime (52.5 g) was dissolved in petroleum ether, boiling point range 50°–110° C. (250 mL), in a 500 mL 3-necked flask and methyl trichlorosilane (15 g) in petroleum ether (100 mL) was slowly added with stirring starting at 25° C. When the mixing was complete (20 min) the final temperature was 38° C. The two-phase system was then heated with stirring at a maximum of 67° C. for 1½ hours. After cooling to ambient, the two phases were separated.

The bottom phase (38 g) was mixed with more petroleum ether (250 mL) and with stirring treated with ammonia gas when a voluminous precipitate of ammonium chloride was formed. On filtration a clear filtrate was collected which contained methyl ethyl ketoxime in petroleum ether (as determined by gas chromatography), suitable for reuse.

The top phase was separately treated with ammonia gas and filtered. The filtrate was distilled at reduced pressure (120° C. pot temperature at 1 mm Hg or 133 Pa) to remove all the solvent and any methyl ethyl ketoxime. The liquid residue in the distillation flask (28 g, yield 93.0%) was colorless and was found to be pure methyl tris-(methyl ethyl ketoximo)silane.

EXAMPLE 7

Reaction of MEKO with MTCS (6:1)

In a 500 mL 3-necked flask was placed a solution of methyl ethyl ketoxime (52.5 g) in dry petroleum ether (50°–110° C.; 250 mL). After heating to 45° C., methyl trichlorosilane (15 g) in 100 mL petroleum ether was added slowly (20 minutes). Temperature rose to 55° C. Heating was continued for 1½ hours at a maximum of 67° C. The reaction mixture contained two distinct liquid phases. After cooling down to 5° C. in ice bath, ammonia gas was bubbled without separating the phases. Voluminous precipitate of ammonium chloride separated out. This was filtered off, and the clear filtrate was subjected to distillation under reduced pressure to remove low-boiling components (90°–95° C. pot temperature at 2 mm Hg or 267 Pa).

The liquid left in the distillation flask was colorless mobile liquid identified as methyl tris(methyl ethyl ketoximo)silane. Yield 26.7 g (88.7%).

EXAMPLE 8

Reaction of MEKO with Vinyl Trichlorosilane (6.9:1)

Methyl ethyl ketoxime (60 g) in petroleum ether 50°–110° C. (150 mL) was placed in a 300 mL 3-necked flask fitted with condenser, thermometer and dropping funnel. With stirring using a magnetic stirring bar, vinyl trichlorosilane (16.2 g) in petroleum ether (50 mL) was added slowly without any external cooling. The reaction mass temperature rose to 36° C. by the end of the addition, and was heated for 2 hours at 60° C. It was then cooled to ambient temperature and phases were separated. The bottom phase was mixed with more petroleum ether (75 mL) and again phase separated. The petroleum ether phase was mixed with the top phase from the first step.

The total petroleum ether solution was treated with ammonia gas to produce a light white precipitate. This was filtered off and the filtrate distilled, first at atmospheric pressure when most of the petroleum ether was recovered. Finally it was distilled under vacuum (5 mm Hg or 667 Pa) at a maximum of 100° C. pot temperature.

The liquid left in the distillation flask (30 g, yield 95.8%) was very light amber in color. Carbon-13 NMR analysis of this showed that it was pure vinyl tris(methyl ethyl ketoximo)silane.

EXAMPLE 9

Reaction of MEKO with Dimethyl Dichlorosilane (4.9:1)

In a 500 mL 3-necked flask fitted with thermometer, condenser and dropping funnel was placed a solution of methyl ethyl ketoxime (129 g) in hexane (120 g). With stirring dimethyl dichlorosilane (43 g) was added slowly (15 minutes), when the temperature rose to 50° C. The two-phase system was heated with stirring at 65° C. for 2 hours, and then cooled to 23° C. and phases separated.

The top phase (190 g) was treated with ammonia gas from a cylinder, and a light white precipitate separated. This was readily filtered off; and the filtrate (178 g) was subjected to distillation under reduced pressure (2 mm Hg or 267 Pa), to collect pure dimethyl tris-(methyl ethyl ketoximo)silane (69 g, 90.0% yield) as clear, colorless mobile liquid. The identity and purity of the product was determined by Carbon-13 and proton NMR.

The bottom phase (100 g) was neutralized with 50% aqueous NaOH (56 g) after diluting with water (200 g), and methyl ethyl ketoxime was collected as the top phase (69 g).

EXAMPLE 10

Reaction of MEKO with Trimethyl Chlorosilane (2.1:1)

In a 500 mL 3-necked flask fitted with thermometer, condenser and dropping funnel was placed MEKO (74 g) in hexane (125 g). With stirring addition of trimethyl chlorosilane (43.6 g) was started at 23° C. When addition was complete (10 minutes), the temperature was 42° C. It was then heated for 2 hours at 65° C. with stirring. The two phases were separated out after cooling down to 25° C.

The bottom phase (57 g) was neutralized with aqueous NaOH to produce methyl ethyl ketoxime (39 g). The hexane phase containing the product was treated with ammonia gas, filtered and the filtrate distilled. Hexane was mostly removed at atmospheric pressure, and then the remainder distilled to collect a colorless, mobile liquid fraction (58.7 g, 91.9% yield). This liquid was identified by NMR (Carbon-13 and proton) as trimethyl (methyl ethyl ketoximo) silane.

EXAMPLE 11

Reaction of Acetoxime with Methyltrichlorosilane (7:1)

In a 500 mL 3-necked flask fitted with a thermometer and condenser was placed a solution of acetoxime (51 g; 0.7 mol) in hexane (200 g). The solution was heated to distill over 50 g of distillate, thus removing all the water in the acetoxime. A sample of 50 g fresh hexane was added and to the solution at 50° C. was added from a dropping funnel methyl trichlorosilane (15 g; 0.1 mol) with stirring over 10 minutes (temp. 55° C.). With stirring the reaction mixture was heated at 65°–70° C. for 2 hours, when a granular white solid of acetoxime hydrochloride separated out.

The clear hexane solution of the product was separated from the solid by filtration, and subjected to treatment with ammonia gas. No solid separated out indicating that no oxime hydrochloride was present in that phase. It was then distilled to remove hexane first and then acetoxime. Finally the product was collected as a clear, colorless liquid distilling at 110° C. at 2 mm Hg (22.4 g; 86.4% yield).

$^{13}C$ and proton NMR characterized the product as pure methyl tris-(acetoximo)silane.

EXAMPLE 12

Reaction of Cyclohexanone Oxime with Methyltrichlorosilane (7:1)

Cyclohexanone oxime (80 g; 0.7 mol) was placed in a 500 mL 3-necked flask fitted with a thermometer and condenser, and petroleum ether (50°–100° C. boiling range, 200 g) was added to it. It was heated to distill off 67 g of petroleum ether with all the water in the mixture. Fresh petroleum ether (67 g) was then added and then with the solution at 40° C., methyl trichlorosilane (15 g; 0.1 mol) was introduced slowly (10 minutes). With stirring it was heated at 65° C. for 2 hours more. Then a large amount of white precipitate of cyclohexanone oxime hydrochloride separated out.

After cooling to ambient temperature and filtering to remove the solid, the virtually colorless filtrate was treated with ammonia gas. Virtually no solid was formed and the clear solution was distilled first to remove the solvent and then some solid cyclohexanone oxime. The product was finally collected, after heating at 105° C. (pot temperature) at 1 mm Hg for 3 hours, as a virtually colorless, viscous liquid (30.6 g; 80.7% yield).

The product was characterized as methyl tris-(cyclohexanone oxime) silane by $^{13}C$ and $^1H$ NMR analyses.

What is claimed is:

1. A process for the production of Group IVa metal oximates which comprises:
    reacting in the liquid phase a Group IVa metal halide of the formula $P_{4-n}MX_n$ with an oxime compound of the formula R'R"C=NOH, at a mole ratio of oxime compound to Group IVa metal halide of at least 2n:1;
    separating the product of the formula

    (R'R"C=NO)$_n$MR$_{4-n}$ from the by-product oxime hydrohalide of the formula R'R"C=NOH.HX by separating a liquid organic phase consisting essentially of the product from a phase consisting essentially of oxime hydrohalide;
    reacting the liquid organic phase consisting essentially of the product with dry base to convert oxime hydrohalide impurity to oxime compound and solid salt;
    removing the solid salt from the remaining liquid;
    distilling the remaining liquid to remove any unreacted oxime compound and any oxime compound formed upon reaction with dry base; and
    recovering the product as the bottom after distillation;
    wherein R is alkyl of 1–6 carbons, alkenyl of 2–6 carbons, aryl, aralkyl, cycloalkyl or halogen-substituted forms thereof; M is Si, Ge or Sn; X is Cl, Br or I; n is 1 to 4; and R' and R" are each independently H, alkyl of 1–6 carbons, aryl, cycloalkyl, aralkyl or any of them substituted by halogen, or R' and R" are together (CH$_2$)$_m$ wherein m is 3 to 7, or alkyl or halosubstituted forms thereof.

2. The process of claim 1 wherein M is Si.
3. The process of claim 2 wherein X is Cl.
4. The process of claim 3 wherein n is 3.
5. The process of claim 1 or 2 or 3 or 4 wherein R is alkyl of 1–6 carbons.
6. The process of claim 5 wherein R is methyl.
7. The process of claim 1 or 2 or 3 or 4 wherein R is vinyl.
8. The process of claim 1 wherein R' is methyl and R" is ethyl.
9. The process of claim 1 wherein R' and R" are each methyl.
10. The process of claim 1 wherein R' and R" are together (CH$_2$)$_5$.
11. The process of claim 1 or 2 or 3 or 4 wherein said mole ratio of oxime compound to Group IVa metal halide is between about 2n:1 and about 2.2n:1.
12. The process of claim 1 wherein said dry base is ammonia and said solid salt is a solid ammonium salt.
13. The process of claim 1 wherein the phase consisting essentially of oxime hydrohalide is then reacted with ammonia to form solid ammonium halide and oxime compound.
14. The process of claim 1 wherein the phase consisting essentially of oxime hydrohalide is then reacted with aqueous base to form a two-phase system of a first phase consisting essentially of oxime compound and a second phase consisting essentially of water and the halide salt of said base.
15. The process of claim 14 wherein the first phase consisting essentially of oxime compound is separated from the second phase consisting essentially of water and the halide salt of said base; and the first phase is dried to a water level less than 1,000 ppm and recycled to said reacting step.
16. The process of claim 1 wherein a volatile, inert organic solvent is present in the reaction mixture, is present in the liquid organic phase and in the remaining liquid and is removed with the oxime compound by distilling.

* * * * *